United States Patent
Orona et al.

(10) Patent No.: US 10,476,921 B2
(45) Date of Patent: Nov. 12, 2019

(54) SYSTEM EVENT NOTIFICATION

(71) Applicant: CareFusion 303, Inc., San Diego, CA (US)

(72) Inventors: Martin Orona, San Diego, CA (US); Aron Weiler, San Diego, CA (US)

(73) Assignee: CareFusion 303, Inc., San Diego, CA (US)

( * ) Notice: Subject to any disclaimer, the term of this patent is extended or adjusted under 35 U.S.C. 154(b) by 468 days.

(21) Appl. No.: 13/916,472

(22) Filed: Jun. 12, 2013

(65) Prior Publication Data
US 2014/0372522 A1    Dec. 18, 2014

(51) Int. Cl.
| | | |
|---|---|---|
| *H04L 29/06* | (2006.01) | |
| *H04L 29/08* | (2006.01) | |
| *G06F 19/00* | (2018.01) | |
| *G16H 40/20* | (2018.01) | |

(52) U.S. Cl.
CPC ........ *H04L 65/403* (2013.01); *G06F 19/3418* (2013.01); *G16H 40/20* (2018.01); *H04L 67/26* (2013.01)

(58) Field of Classification Search
CPC ...... G06F 7/00; G06F 19/327; G06F 19/3418; A61M 31/00; H04W 4/22; H04W 4/02; G06Q 50/24; H04L 67/12; H04L 67/26; H04L 65/403; H04L 65/40; H04L 67/306; A61B 5/0022; G16H 40/20
USPC ................. 705/2; 709/220; 455/456.3, 404.1
See application file for complete search history.

(56) References Cited

U.S. PATENT DOCUMENTS

| | | | |
|---|---|---|---|
| 6,751,657 B1* | 6/2004 | Zothner | 709/220 |
| 7,155,729 B1* | 12/2006 | Andrew et al. | 719/318 |
| 7,301,451 B2 | 11/2007 | Hastings | |
| 8,775,196 B2 | 7/2014 | Simpson et al. | |
| 8,894,631 B2 | 11/2014 | McTaggart et al. | |
| 8,961,461 B2 | 2/2015 | Stewart et al. | |
| 9,098,604 B2 | 8/2015 | Treacy | |
| 9,356,888 B2 | 5/2016 | Gross et al. | |
| 2002/0087113 A1* | 7/2002 | Hartlaub | 604/65 |
| 2004/0068481 A1* | 4/2004 | Seshadri et al. | 707/1 |

(Continued)

FOREIGN PATENT DOCUMENTS

JP        2001-282922 A    10/2001

*Primary Examiner* — Davoud A Zand
*Assistant Examiner* — Kristoffer L S Sayoc
(74) *Attorney, Agent, or Firm* — Mintz Levin Cohn Ferris Glovsky and Popeo, P.C.

(57) ABSTRACT

The subject matter disclosed herein provides methods for distributing notifications to a user. The method can include receiving data encapsulating notifications from a device connected to a network that provide information relating to the device's status. The device can provide a health related treatment. The method can associate each notification with one or more notification categories relating to a function performed by the device or a location of the device. A table of users having one or more subscriptions to these notification categories can be accessed. The subscriptions can be automatically assigned to users based on the users' role. A user can be identified from the table to distribute the one or more notifications to. The user can have a subscription that matches a notification category of the received notifications, and data comprising the notifications can be distributed to the user. Related apparatus, systems, techniques, and articles are also described.

19 Claims, 5 Drawing Sheets

(56) References Cited

U.S. PATENT DOCUMENTS

| | | | |
|---|---|---|---|
| 2004/0249674 A1* | 12/2004 | Eisenberg | G06Q 10/10 |
| | | | 705/2 |
| 2006/0154642 A1* | 7/2006 | Scannell, Jr. | A01G 9/02 |
| | | | 455/404.1 |
| 2008/0155454 A1 | 6/2008 | Balasubramanian | |
| 2009/0174550 A1* | 7/2009 | Aninye | G07C 9/00111 |
| | | | 340/539.13 |
| 2011/0072379 A1* | 3/2011 | Gannon | A61M 5/172 |
| | | | 715/771 |
| 2011/0078145 A1 | 3/2011 | Chung et al. | |
| 2011/0290250 A1* | 12/2011 | Olson | A61B 5/0836 |
| | | | 128/203.14 |
| 2012/0166530 A1 | 6/2012 | Tseng | |
| 2014/0032694 A1* | 1/2014 | Cohn | G06F 11/3072 |
| | | | 709/207 |
| 2014/0085076 A1* | 3/2014 | Carnes | A61B 5/0022 |
| | | | 340/502 |

* cited by examiner

| Priority | |
|---|---|
| High Priority | ——405 |
| Low Priority | ——410 |

400

| Notification Category | Status | Date/Time |
|---|---|---|
| High Priority | | |
| Intensive Care Unit | Ventilator B has connected to the network | 2-Feb-12/2:13 |
| Low Priority | | |
| Emergency Room | Refill infusion pump A with medication | 2-Feb-12/7:05 |
| Data Set Review | Data set C waiting for review | 31-Jan-12/13:50 |

450

SYSTEM EVENT NOTIFICATION

TECHNICAL FIELD

The subject matter described herein relates to the distribution of notifications from various devices connected to a computing network in a healthcare environment.

BACKGROUND

A hospital computing network can facilitate communication between medical devices, clients, servers, and the like. Medical devices can transfer treatment related information to healthcare providers over the network. Clients can exchange messages with other clients and push data sets to medical devices over the network. Servers can host applications used by clients connected to the network.

As the number of devices connected to the network grows, the number of messages that are exchanged across the network can rapidly increase. This increase in message traffic can inundate recipients with notifications. While some of these notifications can provide important information to a recipient, many of these notifications may be irrelevant or marginally useful.

SUMMARY

In some implementations, methods and apparatus, including computer program products, and systems are provided for the distribution of notifications to a user based on the user's subscriptions to various notification categories.

In one aspect, data encapsulating one or more notifications from a device is received by at least one data processor via a network. The one or more notifications provide information relating to a status of the device. The device is connected to the network and configured to provide a health related treatment for a patient. In addition, each of the one or more notifications is associated, by at least one data processor, with one or more notification categories. The one or more notification categories relate to a function performed by the device or a location of the device. A table of one or more users is accessed by at least one data processor. Each of the one or more users has one or more subscriptions to the one or more notification categories. The one or more subscriptions are automatically assigned to the one or more users based on a role associated with the one or more users. At least one user is identified, by at least one data processor, from the table to distribute the one or more notifications. The at least one user has at least one subscription that matches at least one notification category of the one or more notifications. Data comprising the one or more notifications are distributed to the at least one user by at least one data processor.

The above methods, apparatus, computer program products, and systems can, in some implementations, further include one or more of the following features.

The distributing can include at least one of loading the one or more notifications on a notifications page associated with the at least one user, sending an e-mail containing the one or more notifications to the at least one user, and sending a text message containing the one or more notifications to the at least one user. The one or more notification categories for the at least one user can be associated by at least one data processor with at least a high priority and a low priority. The notifications page can display notifications in a notification category associated with a high priority before notifications in a notification category associated with a low priority.

The role associated with the one or more users can be based on a position or a department associated with the one or more users.

The status of the device can indicate whether the device is connected to the network. The status of the device can specify whether action is required from the at least one user.

The device can be selected from a group consisting of an infusion pump, a ventilator, an electrocardiogram, and a computing device hosting a data set editor application. The action required by the notification sent from the infusion pump can indicate that the infusion pump needs to be refilled with medication. The action required by the notification sent from the computing device can indicate that a data set generated by the data set editor application is awaiting review.

In some implementations, at least one of the subscriptions automatically assigned to the at least one user can be automatically deleted by at least one data processor when the role associated with the at least one user changes.

A removal request from the at least one user for at least one of the subscriptions can be received by at least one data processor. The at least one subscription can be deleted by at least one data processor.

The one or more notifications can be modified by at least one data processor before the one or more notifications are distributed. These modifications can include the addition of information to the one or more notifications. This information can include when the one or more notifications was received.

Computer program products are also described that comprise non-transitory computer readable media storing instructions, which when executed one or more data processors of one or more computing systems, causes at least one data processor to perform operations herein. Similarly, computer systems are also described that may include one or more data processors and a memory coupled to the one or more data processors. The memory may temporarily or permanently store instructions that cause at least one processor to perform one or more of the operations described herein. In addition, methods can be implemented by one or more data processors either within a single computing system or distributed among two or more computing systems. Such computing systems can be connected and can exchange data and/or commands or other instructions or the like via one or more connections, including but not limited to a connection over a network (e.g. the Internet, a wireless wide area network, a local area network, a wide area network, a wired network, or the like), via a direct connection between one or more of the multiple computing systems, etc.

The subject matter described herein provides many advantages. For example, in some implementations, the current subject matter can allow notifications to be distributed to users based on the users' subscriptions to various notification categories. In addition, the current subject matter can allow a user to assign a priority level to each notification category. The display of these notifications can be customized based on these priority levels.

The details of one or more variations of the subject matter described herein are set forth in the accompanying drawings and the description below. Other features and advantages of the subject matter described herein will be apparent from the description and drawings, and from the claims.

DESCRIPTION OF DRAWINGS

The accompanying drawings, which are incorporated herein and constitute a part of this specification, show certain aspects of the subject matter disclosed herein and, together with the description, help explain some of the principles associated with the subject matter disclosed herein. In the drawings.

Like reference symbols in the various drawings indicate like elements.

DETAILED DESCRIPTION

The subject matter disclosed herein relates to the distribution of notifications to a user based on the user's subscriptions to various notification categories. In some implementations, these notifications can be associated with notification categories that relate to a function performed by a device that sent the notification or a location of the device that sent the notification.

Figure 1:
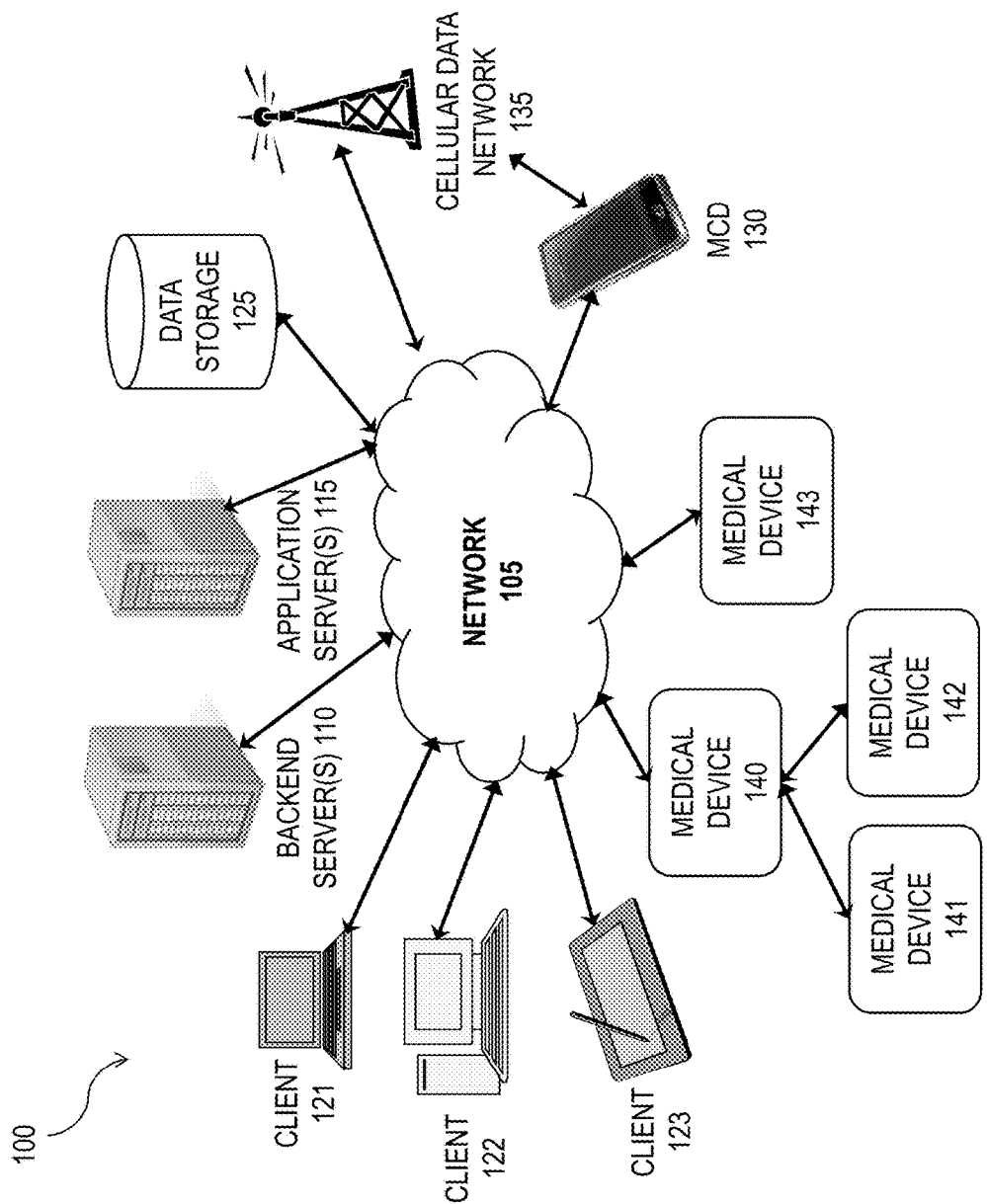
FIG. 1 is a system diagram illustrating a computing landscape within a healthcare environment.

FIG. 1 is a system diagram illustrating a computing landscape 100 within a healthcare environment such as a hospital. Various devices and systems, both local to the healthcare environment and remote from the healthcare environment, can interact via at least one computing network 105. This computing network 105 can provide any form or medium of digital communication connectivity (i.e., wired or wireless) amongst the various devices and systems. Examples of communication networks include a local area network ("LAN"), a wide area network ("WAN"), and the Internet. In some cases, one or more of the various devices and systems can interact directly via peer-to-peer coupling (either via a hardwired connection or via a wireless protocol such as Bluetooth or WiFi). In addition, in some variations, one or more of the devices and systems communicate via a cellular data network.

In particular, aspects of the computing landscape 100 can be implemented in a computing system that includes a back-end component (e.g., as a data server 110), or that includes a middleware component (e.g., an application server 115), or that includes a front-end component (e.g., a client computer 121 having a graphical user interface or a Web browser through which a user may interact with an implementation of the subject matter described herein), or any combination of such back-end, middleware, or front-end components. Clients 121, 122, and 123 and servers 110 and 115 are generally remote from each other and typically interact through the communications network 105. The relationship of the clients 121-123 and servers 110 and 115 arises by virtue of computer programs running on the respective computers and having a client-server relationship to each other. Clients 121-123 can be any of a variety of computing platforms that include local applications for providing various functionality within the healthcare environment. Example clients include, but are not limited to, desktop computers, laptop computers, tablets, and other computers with touch-screen interfaces. The local applications can be self-contained in that they do not require network connectivity and/or they can interact with one or more of the servers 110 and 115 (e.g., a web browser).

A variety of applications can be executed on the various devices and systems within the computing landscape such as electronic health record applications, medical device monitoring, operation, and maintenance applications, scheduling applications, data set editor applications, billing applications, and the like.

The network 105 can be coupled to one or more data storage systems 125. The data storage systems 125 can include databases providing physical data storage within the healthcare environment or within a dedicated facility. In addition, or in the alternative, the data storage systems 125 can include cloud-based systems providing remote storage of data in, for example, a multi-tenant computing environment. The data storage systems 125 can also comprise non-transitory computer readable media.

Mobile communications devices (MCDs) 130 can also form part of the computing landscape 100. The MCDs 130 can communicate directly via the network 105 and/or they can communicate with the network 105 via an intermediate network such as a cellular data network 135. Various types of communication protocols can be used by the MCDs 130 including, for example, messaging protocols such as SMS and MMS.

Various types of medical devices 140, 141, 142, and 143 can be used as part of the computing landscape 100. These medical devices 140-143 can comprise, unless otherwise specified, any type of device or system with a communications interface that characterizes one or more physiological measurements of a patient and/or that characterize treatment of a patient. In some cases, the medical devices 140-143 communicate via peer to peer wired or wireless communications with another medical device (as opposed to communicating with the network 105). For example, the medical device 140 can comprise a bedside vital signs monitor that is connected to medical devices 141 and 142, namely a wireless pulse oximeter and to a wired blood pressure monitor. One or more operational parameters of the medical devices 140-143 can be locally controlled by a clinician, controlled via a clinician via the network 105, and/or they can be controlled by one or more of a server 110 and/or 115, clients 121-123, MCDs 130, and/or another medical device.

Application server 115 can run a system event notification application that distributes notifications sent from medical devices 141-143, clients 121-123, MCDs 130, or backend server 110 to various devices connected to network 105. These notifications can provide information relating to a function provided by a particular device or the status of the device. For example, a pharmacist can use one of client computers 121-123 to create or modify a data set using a data set editor application. This data set can contain device configurations, drug libraries, clinical advisories and other important information for medical devices 140-143. The system event notification application can send data encapsulating a notification to various care providers to solicit comments or approval of the data set before the data set is deployed to medical devices 140-143. In another example, medical devices 140-143 can collect data characterizing one or more physiological measurements of a patient and/or treatment of a patient (e.g., medical devices 140-143 can be an infusion management system, etc.). Medical devices 140-143 can transmit data encapsulating a notification with these measurements to application server 115 which, in turn, can distribute data comprising this notification to a particular set of users. For example, medical device 140 can correspond to an infusion pump that infuses a patient with medication. As the amount of medication in the infusion pump depletes below a predetermined threshold, the infusion pump can send data encapsulating a notification to application server 115 to indicate that a new supply of medication is needed. Application server 115 can then distribute data comprising this notification to alert the appropriate personnel.

Before notifications are distributed to users, the system event notification application can associate each notification with one or more notification categories. A notification category can be based on different characteristics associated with the notification including, for example, a function performed by the device that sent the notification. For example, the system event notification application can automatically associate messages sent by backend server 110 with an information technology (IT) notification category because the backend server performs IT related functions. If backend server 110, for example, sends a notification to application server 110 that one of its storage devices has failed, then the system event notification application can associate the message with an IT notification category and distribute this notification to users having an IT notification category subscription. In another example, the system event notification application can automatically associate notifications received from a ventilator or electrocardiogram (ECG) machine (e.g., medical device 140) with a cardiopulmonary notification category because the ventilator and ECG machine perform cardiopulmonary functions. As application server 115 receives data measurements from either the ventilator or ECG machine, it can transmit notifications with these measurements to users having a cardiopulmonary notification category subscription.

Alternatively or additionally, the notification category can be based on a location of the device that sent the notification. If, for example, the ECG machine described above is used in the intensive care unit of a hospital, the system event notification application can associate messages sent from the ECG with an intensive care unit notification category. The system event notification application can then transmit notifications from the ECG in the intensive care unit to users having a subscription to an intensive care unit notification category. The association process can be based on other notification categories including, for example, a caregiver team (which associates messages from a particular device with a notification category that identifies the caregivers that monitor the device), configurations settings (which associates messages from a device operating outside of preset guardrails with a notification category that identifies the members of a configurations setting group), and the like.

As described above, the system event notification application can distribute data that includes these notifications to users based on the user's subscriptions to one or more notification categories. These subscriptions can be based on a role performed by the user and can be automatically assigned to a user based on the user's position within a hospital or a department that the user belongs to. Each role can be a container for various permissions associated with the user. These permissions can designate the types of notifications that a user can receive. The system event notification application can be configured to retrieve position and department information and corresponding user permissions from an employee database.

For example, a nurse belonging to the emergency room department of a hospital can be automatically subscribed to a nursing staff notification category and an emergency room notification category. If the nurse leaves the emergency room to work in the intensive care unit, the system event notification program can automatically update the nurse's subscriptions. During this update process, the nurse can be automatically unsubscribed from the emergency room notification category and automatically subscribed to the intensive care unit notification category. In some implementations, the nurse can unsubscribe himself/herself from a notification category by sending a removal request to the system event notification application. The system event notification application can process the removal request and delete the corresponding subscription.

Figure 2:
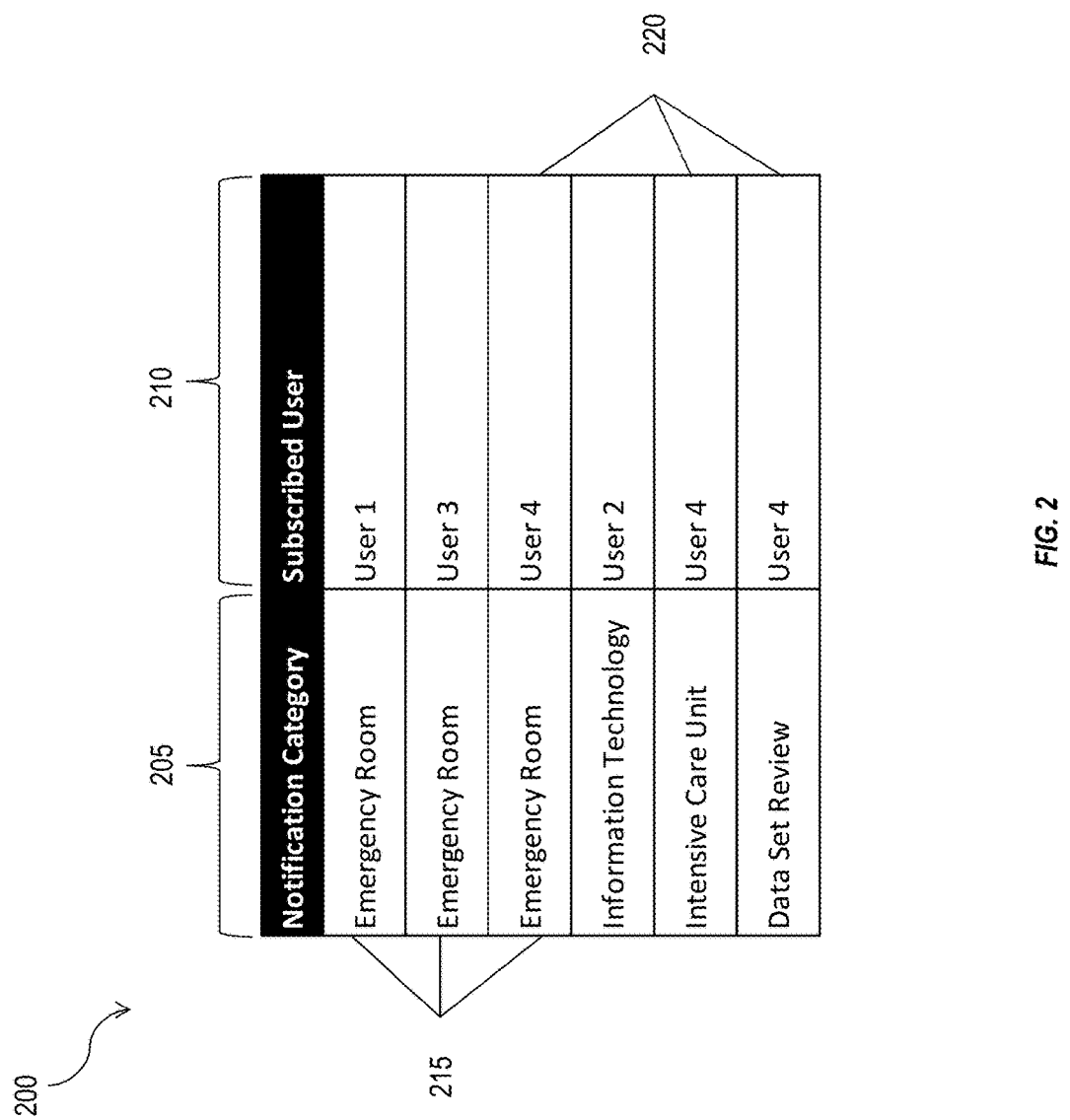
FIG. 2 is a table of notification categories and subscribed users.

FIG. 2 illustrates a table 200 that can be maintained by the system event notification application and stored at data storage systems 125. Table 200 can identify different notification categories (in column 205) used by the system event notification application and the users subscribed to each notification category (in column 210). The system event notification application can update table 200 as users are subscribed and unsubscribed to different notification categories as described above. In addition, the system event notification application can use table 200 to determine which users to send a notification. If, for example, the system event notification application associates a received notification with an emergency room notification category, the application can refer to rows 215 of table 200 to identify the users that have a subscription to this notification category (i.e., user 1, user 3, and user 4) and distribute the notification to these subscribed users. As illustrated in table 200, some users can have multiple subscriptions. For example, as indicated by rows 220, user 4 can receive notifications associated with emergency room, intensive care unit, and data set review notification categories.

Figure 3:
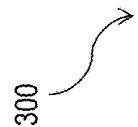
FIG. 3 is a notifications page.

Once the system event notification application has identified which users should receive a particular notification, it can distribute data that includes the notification to these users. The system event notification application can distribute these notifications in their original form or modify them to include less information or additional information. The additional information can include, for example, the date/time that the application server received the notification from the device, and the like. Distribution can occur via different modalities. For example, the system event notification application can send data including the notification to an address associated with the user (e.g., an e-mail address or a text message phone number). In some implementations, these notifications can be displayed on a user's notifications page 300 as illustrated in FIG. 3. A user can access his/her notification page by logging onto the system event notification application using, for example, computer clients 121-123 or MCDs 130.

Notifications page 300 can display all of the notifications for user 4 from table 200. For each of these notifications, notifications page 300 can display the notification category (in column 305), a status associated with the notification (in column 310), and the date/time that the notification was distributed from application server 115 (in column 315). In some implementations, column 315 can also display the date/time that application server 115 received the notification from the originating device. As explained above with respect to FIG. 2, user 4 can have subscriptions to emergency room, intensive care unit, and data set review notification categories, and these notifications can be displayed at rows 320, 325, and 330, respectively.

The status description (in column 310) can provide information regarding the device that sent the notification. This information can include, for example, whether the device is connected to network 105, when the device is turned on, when the device is turned off, and the like. The status description (in column 310) can also indicate whether a notification requires user action. For example, the status associated with notification 320 can indicate that infusion pump A in the emergency room needs to be refilled with medication. This notification can appear on the notifications page of all users that have an emergency room notification category subscription. Once infusion pump A has been refilled, the pump can report its status to application server 115. Upon receiving this status message, the system event notification application can delete the original notification from the notification page of the designated subscribers and/or send a follow-up notification to the subscribers to indicate that action is no longer required. In another example, the status associated with notification 330 can indicate that data set C is awaiting review by user 4. This notification can appear when an entity designates user 4 as a reviewer for data set C and can remain on notifications page 300 until user 4 completes the review.

Figures 4A, 4B:
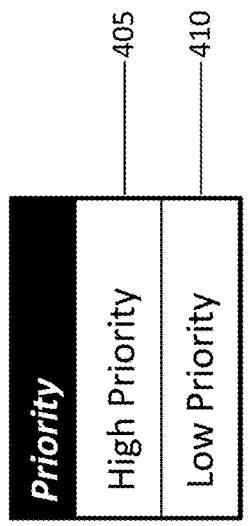
FIG. 4A is a priority assignment window.
FIG. 4B is a notifications page that displays notifications based on the priority associated with various notification categories.

A user can customize his/her notifications page by grouping notifications according to their priority levels. This feature can be useful, for example, when a user has subscriptions to numerous notification categories and wants to review notifications from the most important categories first. The user can designate the relative importance of different notification categories by assigning a priority level to each category. A user can, for example, use window 400 of FIG. 4A to assign a high priority level 405 or a low priority level 410 to a notification category. Window 400 can appear when a user, for example, clicks on or hovers over a notification category 305 on notifications page 300. In the example of FIG. 3, user 4 can use window 400 to assign a high priority level to the intensive care unit notification category and a low priority level to the emergency room and data set review notification categories. Although the implementation of FIG. 4A illustrates two priority levels (i.e., low and high), any number of priority levels can be used (e.g., low, medium, high, and urgent).

As a user assigns priority levels to each notification category, the system event notification program can modify the appearance of notifications page 300. Based on the priority levels assigned by user 4, notifications window 450 in FIG. 4B can display notifications in a high priority notification category (i.e., intensive care unit) before notifications in a low priority notification category (i.e., emergency room and data set review).

Figure 5:
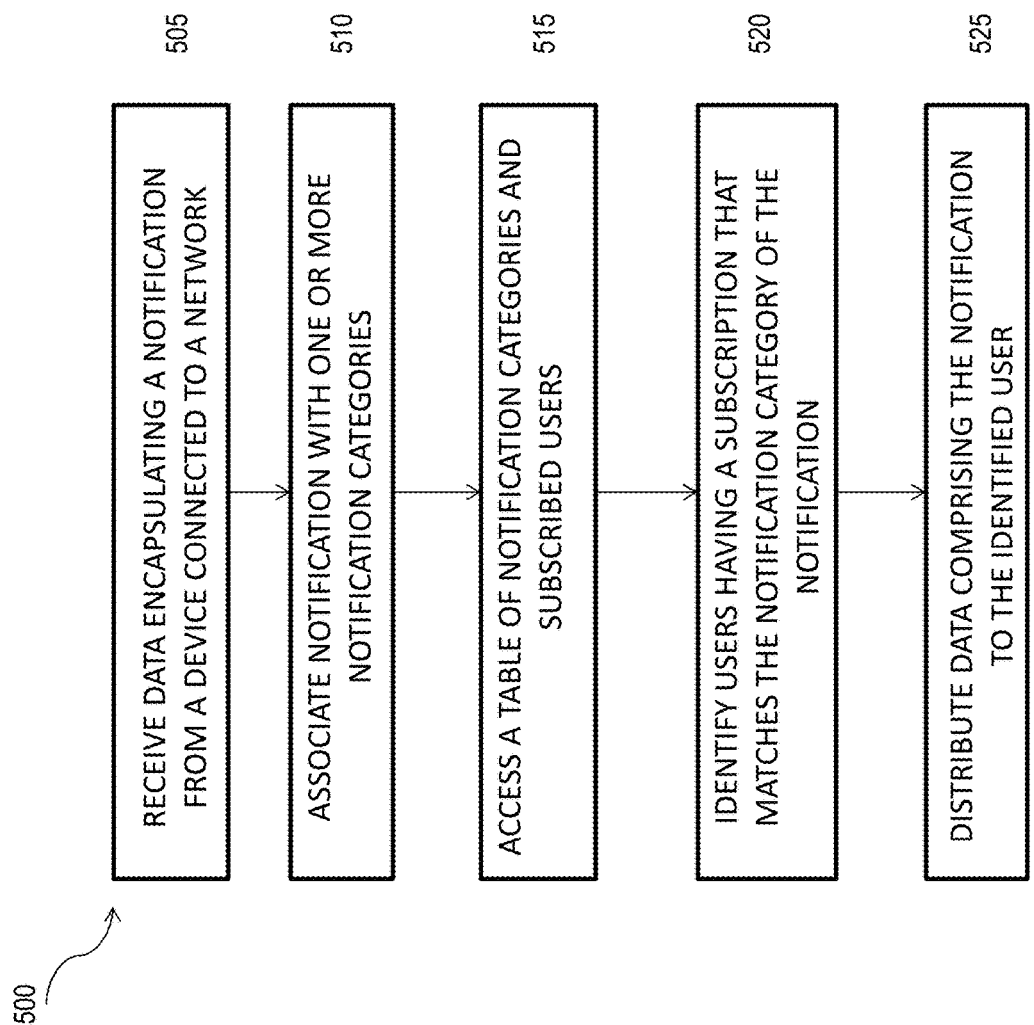
FIG. 5 is a process flow diagram illustrating distribution of notifications to a user based on the user's subscriptions to various notification categories.

FIG. 5 illustrates a flowchart 500 for distributing notifications to a user based on the user's subscriptions to various notification categories. At 505, application server 115 can receive via a network data encapsulating a notification from a device connected to the network. The device can be configured to provide a health related treatment for a patient and can be, for example, any one of medical devices 140-143, clients 121-123, MCDs 130, or backend server 110. In some implementations, the device can be a computing device that hosts a data set editor application that generates data sets to be used by medical devices 140-143. The data encapsulating the notification sent by the device can provide information relating to the status of the device.

At 510, the system event notification application running on application server 115 can associate the notification received at 510 with one or more notification categories. Notification categories can be associated with a function performed by the device that sent the notification. In some implementations, notification categories can be associated with a location of the device that sent the notification.

At 515, the system event notification application can access a table of notification categories and subscribed users. This table can be stored at data storage systems 125 and can identify which users are subscribed to a particular notification category. The system event notification application can automatically assign subscriptions to users based on one or more roles associated with the user. Each of these roles can be associated with various permissions that designate the type of notifications that a user can receive. This role can be based on, for example, the user's position or a department that the user is a member of.

At 520, the system event notification application can identify which users to distribute the notification to. A user can be eligible to receive a notification if he/she has a subscription to the notification category associated with the notification received at 505. The system event notification application can determine whether there is a notification category-user subscription match by referring to the table accessed at 515. If there is a match, then the system event notification application can distribute the notification to the user.

At 525, the system event notification application can distribute data comprising the notification to the users identified at 520. In some implementations, the notification can be loaded onto a notifications page associated with the user or sent to an address associated with the user (e.g., an e-mail address or a text message phone number). In some implementations, the user can assign a priority level to each notification category, and the notifications page can display notifications in accordance with these assigned priority levels.

One or more aspects or features of the subject matter described herein can be realized in digital electronic circuitry, integrated circuitry, specially designed ASICs (application specific integrated circuits), computer hardware, firmware, software, and/or combinations thereof. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device (e.g., mouse, touch screen, etc.), and at least one output device.

These computer programs, which can also be referred to programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, the subject matter described herein can be implemented on a computer having a display device, such as for example a cathode ray tube (CRT) or a liquid crystal display (LCD) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flow(s) depicted in the accompanying figures and/or described herein do not necessarily require the particular order shown, or sequential order, to achieve desirable results. Other implementations may be within the scope of the following claims.

What is claimed is:

1. A method comprising:
   receiving, by at least one processor via a network, data encapsulating a first notification from a medical device connected to the network, the first notification including a physiological measurement of a patient and a status of an infusion pump, the status of the infusion pump specifying that the infusion pump needs to be refilled with medication;
   associating, by the at least one processor, the first notification with a first notification category, wherein the association is based on characteristics associated with the first notification, the first notification category relating to a medical function performed by the medical device and associated with a location of the medical device;
   accessing, by the at least one processor, a table of one or more users including a first user, each of the one or more users having one or more subscriptions to one or more notification categories including the first notification category, the one or more subscriptions assigned to the one or more users based on a plurality of roles including a first role and a second role associated with the one or more users, and further based on locations of the one or more users;
   detecting, by the at least one processor, a change in the first role associated with the first user, the first role associated with a first subscription, the first subscription excluding the first notification, the first subscription assigned to the first user based on the first role;
   updating, by the at least one processor, the first subscription to a second subscription based on the first user being assigned the second role, the second subscription including the first notification including the physiological measurement of the patient;
   identifying, by the at least one processor, the first user from the table of users to distribute the first notification, the first user having the second subscription that matches the first notification category;
   distributing, by the at least one processor, data comprising the first notification including the physiological measurement of the patient to the first user, wherein the data comprising the first notification is populated on a notification page, the notification page customized by the first user based on designations assigned, by the first user, to a plurality of different notification categories including the first notification category, wherein the notification page for the first user comprises a plurality of notifications including the first notification associated with the first user;
   verifying that the infusion pump has been refilled with fluid;
   updating the status of the infusion pump; and
   causing the infusion pump to pump fluid.

2. The method of claim 1, wherein the distributing comprises at least one of sending an e-mail containing the one or more notifications to the at least one user, and sending a text message containing the one or more notifications to the at least one user.

3. The method of claim 1, further comprising:
   associating, by the at least one processor, the plurality of different notification categories for the at least one user with at least a high priority and a low priority, wherein the notifications page displays notifications in a notification category associated with a high priority before notifications in a notification category associated with a low priority.

4. The method of claim 1, wherein the role associated with the one or more users is based on a position or a department associated with the one or more users.

5. The method of claim 1, wherein the status of the medical device indicates whether the medical device is connected to the network.

6. The method of claim 1, wherein the status of the medical device specifies whether action is required from the at least one user.

7. The method of claim 1, further comprising:
   deleting, by the at least one processor, at least one of the subscriptions assigned to the at least one user when the role associated with the at least one user changes.

8. The method of claim 1, further comprising:
   receiving, by the at least one processor, a removal request for at least one of the subscriptions from the at least one user; and
   deleting, by the at least one processor, the at least one subscription.

9. The method of claim 1, further comprising:
   modifying, by the at least one processor, a notification in the one or more notifications before the distributing, the modifying comprising adding information to the notification indicating at least when the notification was received from the medical device.

10. A non-transitory computer-readable medium containing instructions to cause at least one processor to perform operations comprising:

receiving, by at least one processor via a network, data encapsulating a first notification from a medical device connected to the network, the first notification including a physiological measurement of a patient and a status of an infusion pump, the status of the infusion pump specifying that the infusion pump needs to be refilled with medication;

associating, by the at least one processor, the first notification with a first notification category, wherein the association is based on characteristics associated with the first notification, the first notification category relating to a medical function performed by the medical device and associated with a location of the medical device;

accessing, by the at least one processor, a table of one or more users including a first user, each of the one or more users having one or more subscriptions to one or more notification categories including the first notification category, the one or more subscriptions assigned to the one or more users based on a plurality of roles including a first role and a second role associated with the one or more users, and further based on locations of the one or more users;

detecting, by the at least one processor, a change in the first role associated with the first user, the first role associated with a first subscription, the first subscription excluding the first notification, the first subscription assigned to the first user based on the first role;

updating, by the at least one processor, the first subscription to a second subscription based on the first user being assigned the second role, the second subscription including the first notification including the physiological measurement of the patient;

identifying, by the at least one processor, the first user from the table of users to distribute the first notification, the first user having the second subscription that matches the first notification category;

distributing, by the at least one processor, data comprising the first notification including the physiological measurement of the patient to the first user, wherein the data comprising the first notification is populated on a notification page, the notification page customized by the first user based on designations assigned, by the first user, to a plurality of different notification categories including the first notification category, wherein the notification page for the first user comprises a plurality of notifications including the first notification associated with the first user;

verifying that the infusion pump has been refilled with fluid;

updating the status of the infusion pump; and causing the infusion pump to pump fluid.

11. The non-transitory computer-readable medium of claim 10, wherein the role associated with the one or more users is based on a position or a department associated with the one or more users.

12. The non-transitory computer-readable medium of claim 10, wherein the status of the medical device specifies whether action is required from the at least one user.

13. The non-transitory computer-readable medium of claim 10, the operations further comprising:

deleting, by the at least one processor, at least one of the subscriptions assigned to the at least one user when the role associated with the at least one user changes.

14. A system comprising:

a processor; and a memory, wherein the processor and the memory perform operations comprising:

receiving, by at least one processor via a network, data encapsulating a first notification from a medical device connected to the network, the first notification including a physiological measurement of a patient and a status of an infusion pump, the status of the infusion pump specifying that the infusion pump needs to be refilled with medication;

associating, by the at least one processor, the first notification with a first notification category, wherein the association is based on characteristics associated with the first notification, the first notification category relating to a medical function performed by the medical device and associated with a location of the medical device;

accessing, by the at least one processor, a table of one or more users including a first user, each of the one or more users having one or more subscriptions to one or more notification categories including the first notification category, the one or more subscriptions assigned to the one or more users based on a plurality of roles including a first role and a second role associated with the one or more users, and further based on locations of the one or more users;

detecting, by the at least one processor, a change in the first role associated with the first user, the first role associated with a first subscription, the first subscription excluding the first notification, the first subscription assigned to the first user based on the first role;

updating, by the at least one processor, the first subscription to a second subscription based on the first user being assigned the second role, the second subscription including the first notification including the physiological measurement of the patient;

identifying, by the at least one processor, the first user from the table of users to distribute the first notification, the first user having the second subscription that matches the first notification category;

distributing, by the at least one processor, data comprising the first notification including the physiological measurement of the patient to the first user, wherein the data comprising the first notification is populated on a notification page, the notification page customized by the first user based on designations assigned, by the first user, to a plurality of different notification categories including the first notification category, wherein the notification page for the first user comprises a plurality of notifications including the first notification associated with the first user;

verifying that the infusion pump has been refilled with fluid;

updating the status of the infusion pump; and causing the infusion pump to pump fluid.

15. The system of claim 14, wherein the status of the medical device specifies whether action is required from the at least one user.

16. The system of claim 14, the operations further comprising: deleting, by the at least one processor, at least one of the subscriptions assigned to the at least one user when the role associated with the at least one user changes.

17. The method of claim 1, wherein the one or more notification categories are further related to at least a location of the medical device.

18. The method of claim 1, wherein the medical function performed by the medical device includes a cardiopulmonary function.

19. The method of claim 1, wherein said associating the first notification with the first notification category is based at least in part on the medical functions performed by the medical device and the location of the medical device.

\* \* \* \* \*